United States Patent
Davis et al.

(10) Patent No.: US 9,778,299 B2
(45) Date of Patent: Oct. 3, 2017

(54) METHODS AND DEVICES FOR MEASURING COMPOSITIONS OF FLUIDS

(71) Applicants: Thomas A. Davis, El Paso, TX (US); David Nemir, El Paso, TX (US)

(72) Inventors: Thomas A. Davis, El Paso, TX (US); David Nemir, El Paso, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 14/640,632

(22) Filed: Mar. 6, 2015

(65) Prior Publication Data

US 2015/0276836 A1 Oct. 1, 2015

Related U.S. Application Data

(60) Provisional application No. 61/949,155, filed on Mar. 6, 2014.

(51) Int. Cl.
| | |
|---|---|
| *G01N 27/02* | (2006.01) |
| *G01R 27/22* | (2006.01) |
| *C02F 1/00* | (2006.01) |
| *C02F 1/42* | (2006.01) |
| *G01N 27/12* | (2006.01) |

(52) U.S. Cl.
CPC .............. *G01R 27/22* (2013.01); *C02F 1/008* (2013.01); *C02F 1/42* (2013.01); *G01N 27/12* (2013.01); *C02F 2209/055* (2013.01)

(58) Field of Classification Search
CPC ............. G01N 27/302; G01N 27/4165; G01N 27/333; G01N 27/4162; G01N 27/18; G01N 27/403; G01N 27/605; G01N 27/417; G01N 31/221; G01N 2030/345; G01N 2030/645; G01N 2015/0813; G01N 25/18

USPC ....... 324/438, 439, 440, 441, 442, 443, 444, 324/445, 446, 447, 448, 449, 450, 453

See application file for complete search history.

(56) References Cited

U.S. PATENT DOCUMENTS

| | | | | |
|---|---|---|---|---|
| 3,934,193 A | * | 1/1976 | Hall ....................... | G01N 27/06 324/439 |
| 3,964,999 A | * | 6/1976 | Chisdes ............... | B01D 61/025 210/651 |
| 4,032,296 A | * | 6/1977 | Hall ....................... | G01N 27/06 324/446 |
| 4,032,452 A | * | 6/1977 | Davis ................... | B01J 49/0052 204/263 |

(Continued)

FOREIGN PATENT DOCUMENTS

| | | |
|---|---|---|
| DE | 198 38 688 | 3/1999 |
| DE | 19838688 A1 * | 3/1999 ......... A47L 15/4229 |

(Continued)

OTHER PUBLICATIONS

Patent DE 19838688 A1, English Translation. Google Patents.*
International Search Report and Written Opinion in International Application No. PCT/US2015/019167 dated Jul. 8, 2015.

*Primary Examiner* — Patrick Assouad
*Assistant Examiner* — Sean Curtis
(74) *Attorney, Agent, or Firm* — Norton Rose Fulbright US LLP

(57) ABSTRACT

A sensor for detecting the breakthrough of hardness in a water softener measures a change in the conductivity of elongated cation-exchange material in contact with the treated water.

20 Claims, 10 Drawing Sheets

(56) References Cited

U.S. PATENT DOCUMENTS

| | | | | |
|---|---|---|---|---|
| 4,158,628 A * | 6/1979 | Fleckensteim | B01J 49/85 | 210/139 |
| 4,320,010 A * | 3/1982 | Tucci | B01J 49/85 | 210/662 |
| 4,403,039 A * | 9/1983 | Ban | G01N 27/06 | 210/198.2 |
| 4,491,798 A * | 1/1985 | Palmer | B01J 47/14 | 324/425 |
| 4,668,386 A * | 5/1987 | Seal | B01J 47/14 | 210/91 |
| 4,672,322 A * | 6/1987 | Gratteau | G01N 27/07 | 204/400 |
| 4,773,970 A * | 9/1988 | Purbrick | G01N 27/3335 | 204/418 |
| 4,880,513 A * | 11/1989 | Davis | B01J 49/00 | 204/519 |
| 4,935,207 A * | 6/1990 | Stanbro | G01N 27/227 | 422/68.1 |
| 5,078,854 A * | 1/1992 | Burgess | G01N 27/3271 | 204/403.11 |
| 5,322,602 A * | 6/1994 | Razaq | G01N 27/423 | 204/415 |
| 5,491,097 A * | 2/1996 | Ribi | G01N 33/5438 | 422/82.01 |
| 5,990,684 A * | 11/1999 | Merrill | G01N 27/10 | 324/439 |
| 6,258,263 B1 * | 7/2001 | Henderson | G01N 30/6043 | 204/451 |
| 6,712,962 B2 * | 3/2004 | Sugimoto | G01N 30/56 | 210/189 |
| 6,783,684 B2 * | 8/2004 | Teel, Jr. | B01J 49/0095 | 210/190 |
| 7,329,338 B2 * | 2/2008 | Sieth | C02F 1/008 | 210/190 |
| 7,329,346 B2 * | 2/2008 | Liu | G01N 30/62 | 205/789 |
| 7,582,205 B1 * | 9/2009 | Fiscella, Jr. | C02F 1/42 | 210/190 |
| 7,709,265 B2 * | 5/2010 | Chan | A47L 15/4297 | 134/18 |
| 7,780,833 B2 * | 8/2010 | Hawkins | B01D 61/445 | 204/536 |
| 7,872,225 B2 * | 1/2011 | Whitehouse | G01N 30/7266 | 250/288 |
| 7,977,101 B2 * | 7/2011 | Chan | A47L 15/4297 | 436/163 |
| 8,043,507 B2 * | 10/2011 | Liu | G01N 30/62 | 205/789 |
| 8,192,687 B2 * | 6/2012 | Chan | A47L 15/4297 | 422/105 |
| 8,455,817 B2 * | 6/2013 | Whitehouse | G01N 30/7266 | 250/288 |
| 8,487,243 B2 * | 7/2013 | Whitehouse | G01N 30/7266 | 250/288 |
| 8,562,803 B2 * | 10/2013 | Nyberg | B01D 61/44 | 204/536 |
| 8,696,912 B2 * | 4/2014 | Soecknick | C02F 1/008 | 210/434 |
| 8,703,831 B2 * | 4/2014 | Lin | B01D 61/44 | 204/295 |
| 8,784,655 B2 * | 7/2014 | Liu | G01N 30/62 | 205/789 |
| 9,023,902 B2 * | 5/2015 | Lin | B01D 61/44 | 204/295 |
| 9,302,225 B2 * | 4/2016 | Whitehouse | G01N 30/7266 | |
| 2003/0180186 A1 * | 9/2003 | Carson | G01N 33/1853 | 422/82.02 |
| 2005/0202563 A1 * | 9/2005 | Dasgupta | G01N 30/0005 | 436/52 |
| 2006/0231404 A1 * | 10/2006 | Riviello | B01D 61/48 | 204/524 |
| 2007/0108056 A1 * | 5/2007 | Nyberg | B01D 61/44 | 204/554 |
| 2008/0047330 A1 * | 2/2008 | Whitehouse | G01N 30/7266 | 73/61.48 |
| 2008/0116139 A1 * | 5/2008 | Liu | G01N 30/62 | 210/656 |
| 2009/0211980 A1 * | 8/2009 | Liu | G01N 30/26 | 210/659 |
| 2010/0301882 A1 * | 12/2010 | Socknick | C02F 1/006 | 324/694 |
| 2010/0320132 A1 * | 12/2010 | Sakamoto | B01D 61/44 | 210/198.2 |
| 2011/0220789 A1 * | 9/2011 | Whitehouse | G01N 30/7266 | 250/288 |
| 2011/0253606 A1 * | 10/2011 | Chan | A47L 15/4297 | 210/96.1 |
| 2012/0261346 A1 * | 10/2012 | Soecknick | C02F 1/008 | 210/670 |
| 2012/0312178 A1 * | 12/2012 | Hesekamp | B41F 7/26 | 101/147 |
| 2012/0318050 A1 * | 12/2012 | Whitehouse | G01N 30/7266 | 73/61.59 |
| 2014/0048700 A1 * | 2/2014 | Whitehouse | G01N 30/7266 | 250/282 |
| 2014/0069852 A1 * | 3/2014 | Cartwright | C02F 1/442 | 210/96.2 |
| 2014/0076813 A1 * | 3/2014 | Stewart | B01J 47/14 | 210/662 |
| 2014/0238855 A1 * | 8/2014 | Lambert | A61B 5/14542 | 204/403.02 |
| 2014/0332387 A1 * | 11/2014 | Srinivasan | G01N 30/56 | 204/536 |
| 2015/0175459 A1 * | 6/2015 | Hofmann | C02F 5/00 | 137/5 |
| 2015/0276836 A1 * | 10/2015 | Davis | G01R 27/22 | 324/439 |

FOREIGN PATENT DOCUMENTS

| | | | | |
|---|---|---|---|---|
| FR | 2 771 400 | | 5/1999 | |
| FR | 2771400 A1 * | | 5/1999 | A47L 15/4229 |

* cited by examiner

METHODS AND DEVICES FOR MEASURING COMPOSITIONS OF FLUIDS

This application is a non-provisional application claiming priority to U.S. Provisional Patent Application Ser. No. 61/949,155 filed Mar. 6, 2014, which is incorporated herein by reference in its entirety.

BACKGROUND

I. Field of Invention

This invention relates to an apparatus, sensor, and/or method for monitoring the state of an ion-exchange material and in certain aspects the use of that information for water softener control.

II. Background of the Invention

Some water softeners are configured to pass hard water through an ion exchange resin or mineral bed to remove hardness ions from the water. The ion exchange resin or mineral, to a limited extent, also removes dissolved iron through an ion exchange process. The ion exchange resin or mineral bed is recharged to regenerate its hardness and iron removal capability by passing brine through the resin or mineral bed and by backwashing.

The ion-exchange resin or mineral bed is typically regenerated with a brine of NaCl when its ion-exchange capacity is exhausted. An important aspect of the control of a water softener is the determination of when to initiate the regeneration. For most efficient utilization of salt for regenerating and water for rinsing, it is advantageous to initiate regeneration as soon as breakthrough is detected, but existing analytical instruments for measuring hardness in the water are notoriously expensive and time-consuming. The alternative to detecting breakthrough is to make a conservative estimate of when resin exhaustion will occur with calculations based on assumptions of the hardness of the feed water and the quantity of water that has passed through the resin bed. In one approach total daily water usage is estimated and a timer initiates regeneration after the lapse of a certain number of days. The timer does not distinguish days when there is no flow of water from days when there is a high flow, and the softener might be regenerated when little or none of its capacity has been utilized or it might be regenerated long after breakthrough has occurred, resulting in the passage of untreated hard water.

Another approach is to use a flow totalizer, which measures the quantity of water that has been processed by the softener and initiates regeneration when a preselected quantity of water has been processed. Use of the flow totalizer usually results in better salt economy than the timer, but that approach does not account for variation in the hardness of the source water or deterioration in the ion-exchange capacity as the resin ages.

In another approach the electrical conductivity of the resin bed is used to determine the need for regeneration. Utilization of the conductivity measurement is based on the fact that calcium ions are more tightly held by the resin, and consequently the resin is less conductive in the calcium form than in the sodium form. However, the measurement of resin bed conductivity is confounded by two problems. First, the continuity of current flow between resin beads is through point contacts between spheres, so the measured conductivity through the path of resin beads is much lower than the conductivity of the individual beads. Second, the solution between the beads is also conductive, so changes in the conductivity of the solution will affect the measured conductivity by providing a shunt through which electric current flows. A common approach to alleviating these problems is to install multiple pairs of electrodes in the resin bed and compare the measurements. These imbedded probes still suffer from the fact that they rely on an indirect measurement and do not directly detect breakthrough of calcium.

Additional apparatus and methods for detection of breakthrough or exhaustion of a water softener resin are needed.

SUMMARY

Certain embodiments are directed to apparatus, devices, and/or methods for assessing the ionic composition of a solution by measuring the ionic conductivity of an ion-exchange material that is or has been in contact with an electrolyte solution. The ion-exchange material is a continuous material that can be in the form of a membrane, fiber, fiber bundle, or the like that is positioned between two electrodes. In contrast to previously reported methods of measuring the conductivity of a bed of particles, the apparatus, devices, and methods described herein use a continuous ion-exchange material in the sensor to overcome the inaccuracies associated with particle-to-particle contact and the shunt effect of the conductive solution between the particles.

Certain aspects are directed to the measurement and interpretation of conductivity to gain information about the ionic composition of a solution. In certain aspects the solution is an electrolyte solution. In further aspects the electrolyte solution is water. In still a further aspect the water is water that has been treated or is being treated using a water softener device or method.

In certain applications information about the ionic composition of the water treated by a water softener can be used as the basis for control schemes to accurately direct regeneration of a softening column or material when and as needed. A device or method described herein can provide for minimizing the amount of salt and water used for regeneration, thus reducing the amount of spent brine needing disposal or treatment. With a sensor system of the present invention, regeneration is carried out only as needed, resulting in a lower burden on the waste treatment system and a reduced discharge of salt into the environment.

Certain embodiments are directed to a sensor apparatus for measuring conductivity comprising a continuous ion-exchange material and a voltage divider where the ion-exchange material serves as one leg of the voltage divider in order to generate a voltage that is proportional to the conductivity of the ion-exchange material. The ion-exchange material can be a polymer, paper, or plastic that has been modified with ion-exchange groups. In certain embodiments the other leg of the voltage divider is a resistor. In certain aspects the resistor is a thermistor. A thermistor is a type of resistor whose resistance varies significantly with temperature, more so than in standard resistors. Thermistors are widely used as inrush current limiter, temperature sensors (NTC type typically), self-resetting overcurrent protectors, and self-regulating heating elements. Thermistors differ from resistance temperature detectors (RTDs) in that the material used in a thermistor is generally a ceramic or polymer, while RTDs use pure metals. The temperature response is also different; RTDs are useful over larger temperature ranges, while thermistors typically achieve a higher precision within a limited temperature range, typically $-90°$ C. to $130°$ C.

One embodiment is directed to a sensor for measuring conductivity comprising (i) a continuous ion-exchange material, and (ii) a voltage divider wherein the ion-exchange material serves as one leg of a voltage divider in order to generate a voltage that is proportional to the conductivity. In certain aspects the leg of the voltage divider is a resistor, e.g., a thermistor. In a further aspect switches are engaged periodically in a manner to cause said electrical current to flow in either of two directions in said sensor or to remove electrical current flow from said sensor. In other aspects the voltage is latched so as to store a value that is proportional to said conductivity.

Certain embodiments are directed to a sensor for detecting a change in ionic composition of a fluid comprising (i) a first non-conductive plate and a second non-conductive plate configured to form a cavity through which a test fluid flows, (ii) a continuous ion-exchange material positioned within the cavity and in contact with the fluid, (iii) a first electrode in contact with a first portion of the ion-exchange material and a second electrode in contact with a second portion of the ion-exchange material, the first and second electrode being separated by a predetermined distance, and (iv) a device coupled to the ion-exchange material configured for measuring the electrical conductivity across the ion-exchange material. In certain aspects the continuous ion-exchange material is a membrane or fiber. The ion-exchange membrane can be a cation-exchange or an anion-exchange membrane. In certain aspects the non-conductive plates are planar or semicircular. In a further aspect the sensor further comprises a diaphragm positioned in the cavity between a non-conductive plate and the ion exchange material, said diaphragm being configured, upon application of pressure to the diaphragm, to displace fluid between the diaphragm and the ion-exchange material for the purpose of eliminating the fluid as an alternative path for the flow of electric current between the electrodes. In certain aspects the diaphragm is coupled to an actuator. The actuator can be an electrical, hydraulic, pneumatic, or mechanical actuator. In certain aspects the actuator moves the diaphragm to evacuate the sensor cavity. In certain aspects the cavity is opened after a period of time and fluid flows through cavity until the actuator is engaged.

Other embodiments are directed to a water softener system comprising a water softener apparatus fluidically connected to one or more sensors described herein. In certain aspects a sensor is positioned such that a portion of fluid exiting the water softener flows through the sensor. In a further aspect a sensor is positioned such that a portion of fluid flowing through the water softener flows through the sensor during transit through softener.

In a further embodiment a water hardness sensor can comprise (i) a first non-conductive plate and a second non-conductive plate configured to form a cavity through which a test fluid flows, wherein a surface of at least one of the plates facing the cavity is chemically modified to form an ion-exchange surface, (ii) a first electrode in contact with a first portion of the ion-exchange surface and a second electrode in contact with a second portion of the ion-exchange surface, the first and second electrode being separated by a predetermined distance, and (iii) a device for measuring the electrical conductivity across the ion-exchange surface operatively coupled to the first and second electrodes.

In still further embodiments a water hardness sensor can comprise (i) a non-conductive block that forms the housing for the sensor, said block forming a cavity; (ii) two or more ion-exchange fibers forming a fiber bundle are positioned in the cavity, wherein one end of the fiber bundle is in electrical contact with a first electrode and the other end is in electrical contact with a second electrode, the first and second electrode being separated by a predetermined distance, and (iii) and the first and second electrodes connected to a device for measuring the electrical conductivity across the ion-exchange fibers.

Certain embodiments are directed to methods utilizing a sensor as described herein. A method for detecting a change in ionic composition of a fluid can comprise (i) contacting a sensor with a first fluid sample at a first time point, wherein the sensor comprises a continuous ion-exchange material and a resistor in electrical series where voltage across the ion-exchange material is proportional to the electrical conductivity of the ion-exchange material and detecting the voltage across the ion-exchange material at the first time point; (ii) contacting the sensor with a second fluid sample at a second time point and detecting the voltage across the ion-exchange material at the second time point; and (iii) determining the change in ionic composition of the fluid based on the change in voltage across the ion-exchange material. In certain aspects the method can further comprise evacuating the fluid sample from the sensor cavity after a predetermined period of time prior to detecting the voltage across the ion-exchange material.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any system, device, method, or composition of the invention, and vice versa.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
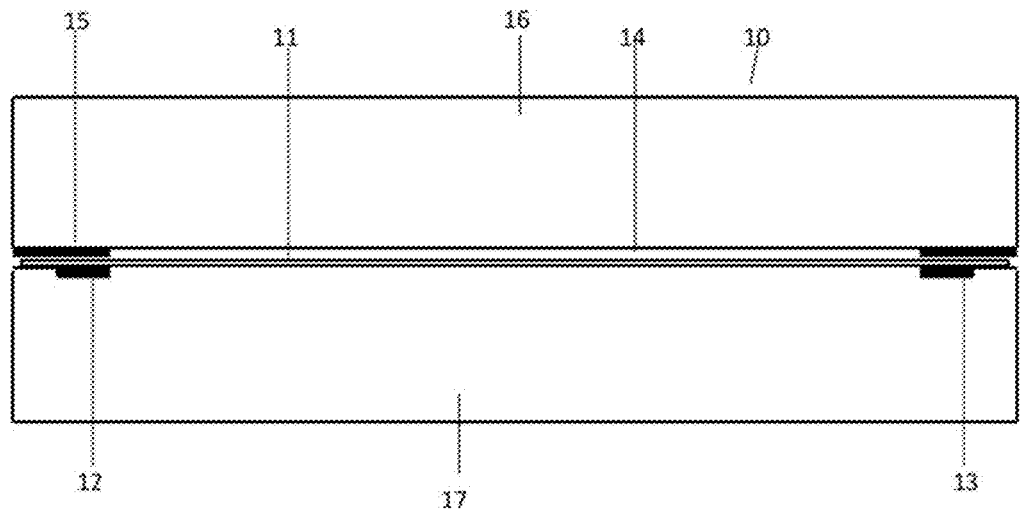
FIG. 1 is a cross-sectional view of a planar sensor of the present invention.

Water softeners can comprise cation-exchange resins that have the ability to take up cations like sodium, potassium, calcium, and magnesium. Typical cation-exchange resins useful in water softeners are prepared by suspension polymerization of monomer styrene and the crosslinking agent divinylbenzene to form polymer beads. The polymer beads are subsequently treated with a sulfonating agent, attaching sulfonic acid groups to the polymer. The sulfonic acid groups impart a negative ionic charge to the cation-exchange beads. When the beads are exposed to a salt solution that negative charge becomes associated with cations in solution. For example, when the beads are exposed to a solution of sodium chloride, the cations in the beads are sodium ions.

Water is said to be "hard" if it has a high concentration (>24 mg/L Ca) of dissolved minerals that are prone to precipitation and producing scale on pipes and fixtures. This scale may be cosmetically objectionable when it is deposited in toilets or sinks Scale can also cause a reduction in diameter in pipes and can hinder heat transfer of heat exchangers by impeding convection and adding to conductive thermal resistance. To avoid mineral deposition dissolved minerals can be removed using cation-exchange resins softening the water. In dilute aqueous solutions, cation-exchange resins of the sulfonated styrene-divinylbenzene type have a strong affinity for calcium and magnesium ions, which are major contributors to water hardness. If resins in the sodium ion form are exposed to hard water, the calcium and magnesium ions enter the resin beads and get exchanged with the sodium ions. When most of the sodium ions have been displaced, the ion-exchange capacity of the resins is said to be exhausted. The ion-exchange capacity of a resin can be regenerated by exposing the resin to a concentrated solution of sodium chloride (i.e., brine). The sodium ions in the brine displace the hardness ions in the resin, and the ion-exchange capacity of the resin is regenerated.

Since calcium is usually the dominant hardness ion in water, calcium is used to represent hardness in the following discussion. It should be understood that the softening process removes other ions including magnesium, strontium, iron, and any other cations that are removed by the cation-exchange resin. A typical water softener apparatus comprise of cation-exchange beads contained in a cylindrical tank. Hard water is allowed to flow downward through the bed of resin beads and calcium ions are removed as the water comes into contact with the beads. The beads at the top of the resin bed become exhausted first, and then the exhaustion proceeds down the bed until the flow is stopped or until the resin is fully exhausted. When the resin bed gets exhausted the condition of breakthrough occurs, and calcium ions appear in increasingly higher concentrations in the treated water.

It is desirable to stop the flow of water and regenerate the resin as soon as an increase in calcium ion concentration is detected in the solution coming out of the tank, i.e. breakthrough, occurs. Regeneration can be done by introducing a concentrated solution of sodium chloride, or brine, from the bottom of the resin bed, a process known as counter-current regeneration. As the brine moves slowly up through the bed, calcium ions are displaced and carried out with the brine. The brine solution produced by regeneration is called spent brine and typically has a high concentration of calcium chloride at the beginning of the regeneration cycle. The calcium ion concentration decreases as regeneration progresses. The spent brine can contain other displaced ions, in addition to sodium and calcium, such as magnesium. Because the resin in the bottom of the bed is being exposed to pure sodium chloride solution, the resin in the bottom of the bed becomes fully regenerated. In some cases the resin in the top of the bed might be only partially regenerated.

After the brine flow is stopped, water is introduced from the top of the resin bed to displace the brine. In certain aspects the water is deionized water. This step is called the slow rinse, and it benefits from the fact that the brine has higher density than the water that is displacing the brine. The slow rinse is followed by a fast rinse to wash out any remaining sodium chloride from the resin bed. The fast rinse is typically at a higher flow rate, e.g., 1 to 1.5 gpm per cubic foot. After the fast rinse the resin bed is ready for the next exhaustion cycle. Typically, a control system governs the operations mentioned. The control system usually sits on top of the cylindrical tank containing the resin. The control system comprises a controller, valves, motors, gears, timers, switches, meters, and circuitry needed to control the sequencing of the operating cycles.

Certain embodiments are directed to methods and apparatus for assessing the ionic composition of an electrolyte solution through the measurement of the ionic conductivity of an ion-exchange material that is in contact with an electrolyte solution. The measurements can be used to determine control actions. In certain aspects the ion-exchange material will be in contact with the processed water coming out of the water softener. When breakthrough occurs, the processed water will begin having a higher concentration of calcium ions, and this will affect the ionic conductivity of the ion-exchange material of the sensor. In some settings, an absolute decrease of ionic conductivity above a preset threshold will be indicative of a resin bed that is becoming exhausted.

There may be multiple sensor inputs available for making decisions as to the initiation of regeneration. These could include multiple ionic conductivity measurements from sensors. These could also include a measurement of flow rate and measurements of one or more of ambient temperature, resin bed temperature, or fluid stream temperature.

Individually, sensor data can be collected over time and then processed in batch to determine a control action. For example, if the ionic conductivity measured by a sensor is changing quickly, that may be indicative of a rapidly exhausting resin bed. In contrast, a slowly changing ionic conductivity, particularly if it correlates with temperature change, may simply be a reflection of aging and/or temperature dependence of the measured conductivity.

I. Sensor Device

Referring now to the invention in more detail, FIG. 1 shows a planar sensor 10 containing an ion-exchange material in the form of membrane 11 with its edges in contact with a pair of electrodes 12 and 13 separated by a prescribed distance. The membrane 11 is exposed to a cavity 14 through which the solution flows across the membrane, that is, either into or out of the page in FIG. 1. Electrodes 12 and 13 are in electrical contact with the membrane 11. A gasket 15 of resilient material serves to press the membrane tightly against the electrodes to ensure the electrical contact. End plates 16 and 17 can be made of non-conductive material and provide the structure for the sensor. In further detail, FIG. 1 shows the simplest arrangement of the components of planar sensor 10. The fluid flowing through cavity 14 is in contact with the membrane 11, and the ions in the fluid exchange with the ions in membrane 11 until a condition of equilibrium is approached. In the case in which the sensor is used as a hardness sensor for a water softener and membrane 11 comprises a cation-exchange material, the fluid would be water containing mostly sodium and calcium ions. Membrane 11 of the sensor would be in contact with water from the discharge of the softener that flows through cavity 14. When the resin bed of the water softener is not near exhaustion, sodium ions are the dominant cations in the water, and consequently sodium ions are the dominant cations in membrane 11. Under this condition membrane 11 is in its most conductive state. The conductivity of membrane 11 is measured by means similar to those used for measuring solution conductivity. Certain aspects use an alternating current of high frequency and low amperage to minimize polarization at the contacts between membrane 11 and electrodes 12 and 13. Measurement of a substantially steady value of membrane electrical conductivity is an indication that the resin bed still has useful softening capacity.

When the resin bed of the water softener approaches exhaustion, calcium ions appear in the discharge stream of a water softener. The calcium ions displace sodium ions in membrane 11, and membrane 11 becomes less conductive, because calcium ions are held more tightly than sodium ions. Measurement of a reduction in the conductivity of membrane 11 provides an indication of breakthrough of calcium. A progressive decrease in conductivity of the membrane is interpreted by the controller as an indication that the resin bed should be regenerated.

The ion-exchange material is illustrated as a membrane sheet in FIG. 1, but the invention includes ion-exchange materials in other forms. The invention includes ion-exchange material in the form of fibers. In certain embodiments the fibers are in electrical contact with the electrodes. The invention can also include the use of hollow fibers or tubes wherein the wall of the fiber or tube comprises ion-exchange material. In certain aspects the fluid to be tested flows through the lumen of the hollow fiber or tube, and the electrodes are positioned at the ends of the hollow fiber or tube.

The ion-exchange material can also be an integral part of one or both of end plates 16 and 17. The invention can include an integral ion-exchange material that is attached to the surface of an end plate by means that include adhesion, fusion, polymerization of monomers on or within the material of the end plate, or functionalization of the polymer of the end plate to form ion-exchange groups on the surface of the plate. In certain aspects an end plate made of poly (vinyl chloride) (PVC) is exposed to the monomers styrene and divinylbenzene, which are absorbed into the surface of the PVC plate. Then the surface of the plate is exposed to a polymerization initiator such as benzoyl peroxide, irradiation, or any other known polymerization initiator or catalyst. After polymerization, the polymer coating is treated with a reagent that produces ion-exchange groups on the polymer. Sulfuric acid is an example of a treatment agent to produce cation-exchange groups on the styrene/divinylbenzene copolymer. In other aspects the surface of the plate includes a polymer that is made from monomers that include styrene. Examples of styrene-containing polymers include poly (acrylonitrile-cobutadiene-co-styrene) (ABS), poly(styrene-isobutylene-styrene) triblock copolymers (SIBS), and styrene butadiene rubber (SBR). The styrene-containing polymer is treated with a sulfonating agent, e.g. sulfuric acid, to impart cation-exchange properties to the surface of the polymer. In any surface treatment of the polymer to impart ion-exchange properties to the surface of the polymer, the thickness of the layer of ion-exchange material can be minimized in order to minimize the distance that ions must diffuse into the surface of the polymer. Reducing the diffusion distance beneficially reduces the response time of the hardness sensor.

Figure 2:
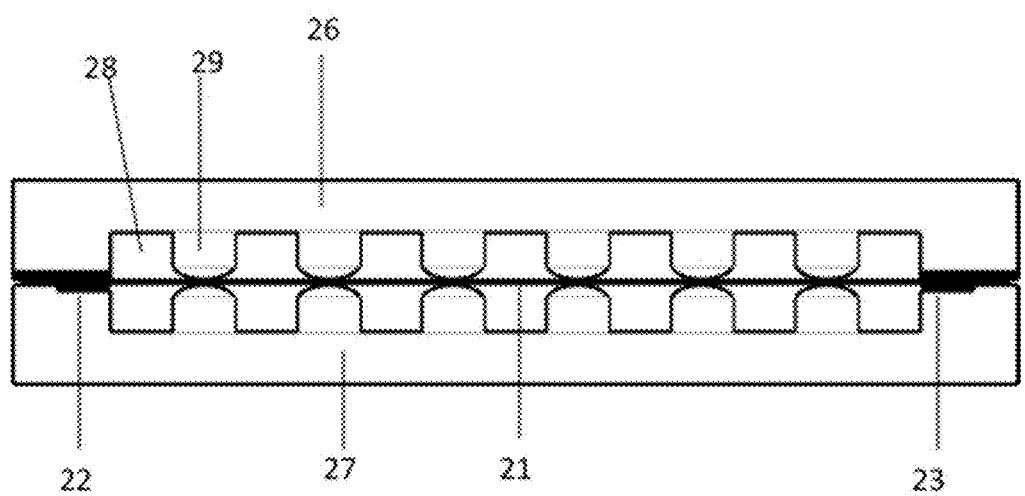
FIG. 2 is a cross-sectional view of a planar sensor of the present invention with ribs.

FIG. 2 shows a planar sensor in which the end plates 26 and 27 contain multiple slots 28 through which the solution flows. The slots are separated by ridges 29 that are close to or touching membrane 21. The ridges serve to interrupt the flow of electric current through the solution between electrodes 22 and 23 by interrupting the fluid path between adjoining slots and thereby reducing the conductivity path between electrodes and through the solution. Ridges 29 can be formed by cutting or molding slots 28 into the end plates or by inserting non-conductive netting with parallel strands, such as the netting supplied by Conwed. Ridges 29 and slots 28 can be on both sides of membrane 21 as shown in FIG. 2, or they can be on only one side of the membrane. A benefit of having ridges 29 and slots 28 on both sides of membrane 21 is that solution can flow on both sides of the membrane 21 and cause faster equilibration of the ion exchange sites in membrane 21. It should be noted that slots 28 serve the function of conveyance of the solution through the sensor to contact the membrane, which is the same function as cavity 14 in FIG. 1.

Figure 3A:
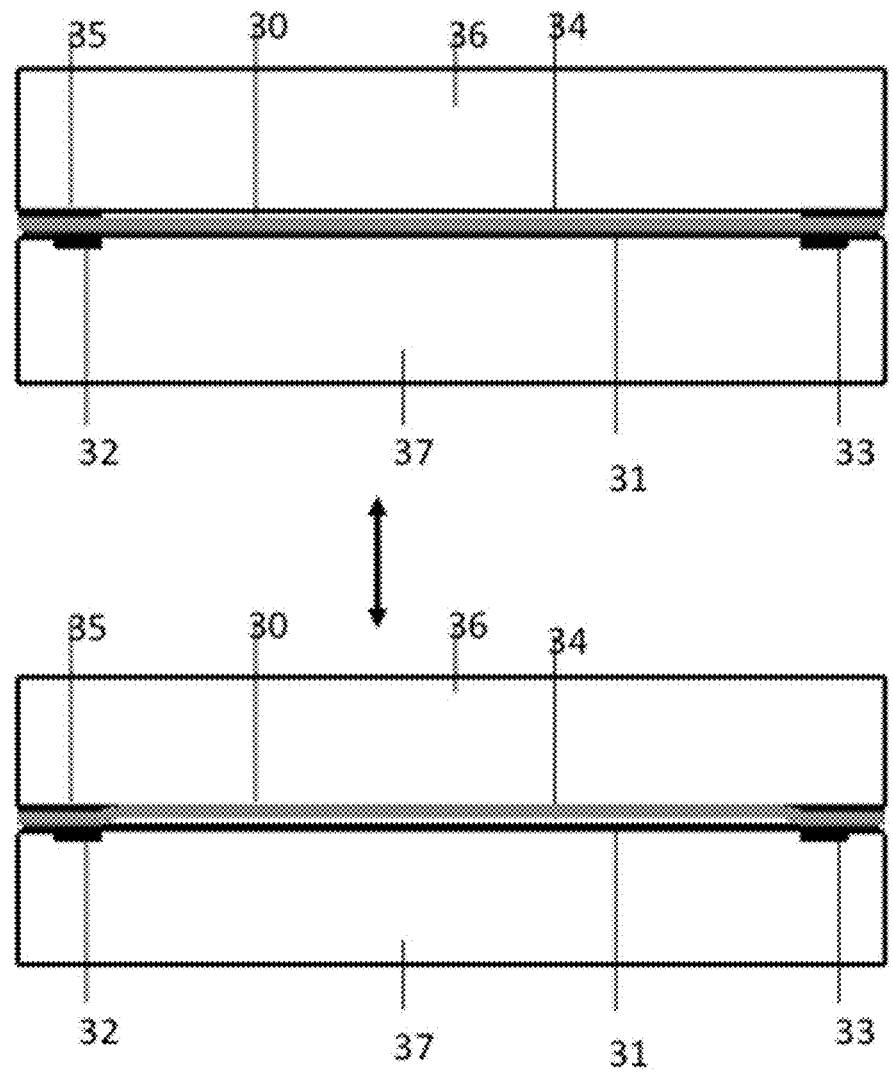
FIG. 3A-3B is a cross-sectional view of a planar sensor of the present invention with a diaphragm.
Figure 3B:
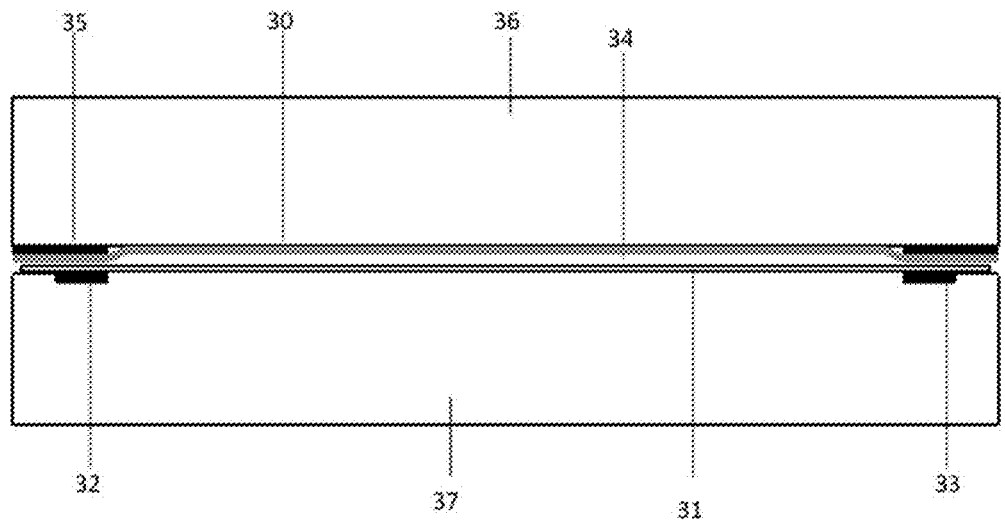

FIG. 3 illustrates a sensor with diaphragm 30 that can be actuated to displace the solution that is in cavity 34 through which the solution flows to contact membrane 31. The device can be configured for actuating the diaphragm. The diaphragm can be actuated using hydraulic pressure, pneumatic pressure, mechanical force or the like, or any means known in the art, for displacing a diaphragm. Activating a diaphragm is just one way of displacing the solution in contact with the membrane. The intent is to remove the solution from the path of measurement of the conductivity of the membrane so that a change in the conductivity of the solution does not impact the measurement. Any means for displacing the solution during the measurement of electrical conductivity is included in the invention. For example, the use of a piston actuated directly or indirectly by a solenoid is means of displacing the solution. A preferred means of actuating diaphragm 30 is to restrict the flow of solution into cavity 34 and divert the solution to the backside of the diaphragm in order to achieve a higher pressure on the backside of the diaphragm than in the cavity. In the operation of the sensor illustrated in FIG. 3, solution flows through cavity 34 to allow exchange of ions between membrane 31 and the solution to be tested. When it is time for a test, solution flow through the cavity 34 is stopped, and diaphragm 30 is actuated so that it is pressed against membrane 31 to displace the solution from cavity 34. Next the membrane conductivity is measured. Finally the actuation of diaphragm 30 is reversed, and solution is allowed to flow through cavity 34. As described earlier, the ion-conductive function of membrane 31 can be replaced by imparting ion-exchange properties to the surface of the end plate 37.

An added benefit of the diaphragm is that it allows the sensor to serve two functions. If the sensor is situated in or connected to the line that conveys solution exiting the resin bed, the sensor is exposed to the treated water during the service cycle of the softener, and it is exposed to the brine and rinse solutions during the regeneration cycle. With a large volume in the cavity, the membrane contributes negligible conductivity of the sensor when the cavity is filled, so the sensor measures the conductivity of the solution. But when the volume of the cavity is displaced by the diaphragm, the conductivity of the membrane is dominant, and the sensor measures the conductivity of the membrane, which reflects the composition of the solution that has been in contact with the membrane. This dual-function sensor is useful in the operation of the water softener, because it can be used to detect when a water softener needs to be regenerated, and it can detect when the brine has been adequately rinsed from the regenerated resin. The benefit of the latter detection is that the flow of rinse water can be stopped as soon as adequate rinsing has been detected rather than after a programmed time of rinsing.

Figure 4:
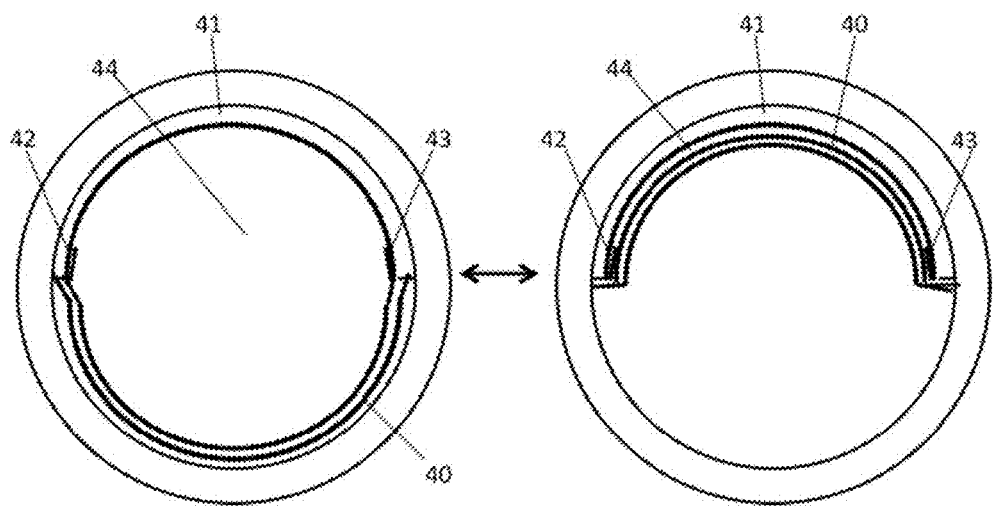
FIG. 4 is a cross-sectional view of a tubular sensor of the present invention.

FIG. 4 illustrates a sensor in a tubular configuration with a semicircular diaphragm 40 that can be actuated to displace the solution that is in cavity 44 through which the solution flows to contact semicircular membrane 41. In certain aspects the device includes an actuator for diaphragm 40. The actuator can act on diaphragm 40 by use of hydraulic pressure, pneumatic pressure, a mechanical force or any other means know in the art for displacing a diaphragm. Electrodes 42 and 43 can be positioned on opposite sides of the tube and attached to the surface of membrane 41 at its edge. When diaphragm 40 is not actuated, as shown on the left view of FIG. 4, the cavity is wide open and ions in the fluid flowing through the cavity equilibrate with ions in membrane 41. Also, since the fluid occupies most of the volume between electrodes 42 and 43, conductivity measured between electrodes 42 and 43 will be an indication of the conductivity of the fluid in cavity 44. When diaphragm 40 is actuated, as shown in the right view, the volume of fluid in cavity 44 is negligible, and conductivity measured between electrodes 42 and 43 will be an indication of the conductivity of the membrane. Therefore, the sensor described in FIG. 4 is a dual-purpose sensor that can be used either to measure the conductivity of the fluid or the conductivity of the membrane, which can be interpreted as an indication of the ionic composition of the solution. When this tubular sensor is exposed to the solution exiting the resin bed of a water softener, it can detect when the softener needs regeneration, and it can detect when the brine has been displaced by rinse water in the regeneration cycle of the water softener. The dual-purpose tubular sensor can be positioned in the bottom of the resin bed, or it can receive a sample of solution that is discharged from the bottom of the resin bed during the exhaustion and regeneration cycles of the resin bed.

Figure 5:
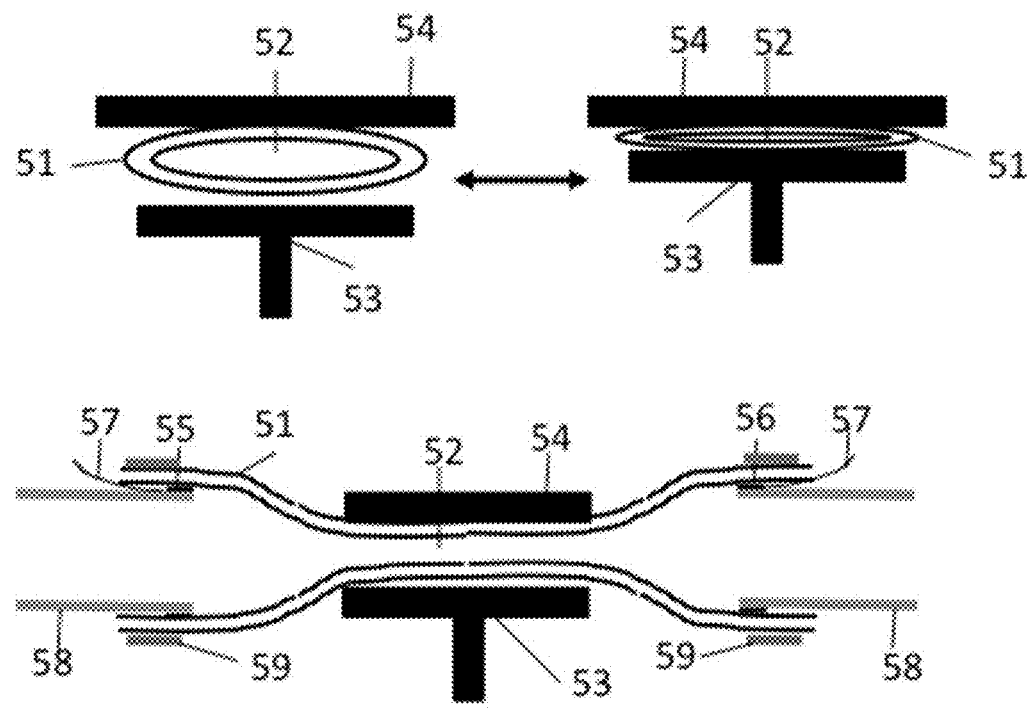
FIG. 5 is a cross-sectional view of a flattened tubular sensor of the present invention.

FIG. 5 illustrates a sensor in a tubular configuration prepared by using a hot platen press to flatten a polymer tube. The inner surface of the flattened polymeric tube 51 is treated chemically to impart cation-exchange properties to the polymer. In a preferred embodiment, the material of the tube is plasticized polyvinyl chloride (PVC), and the inside wall of the tube has been soaked with monomers, e.g., styrene and divinylbenzene, that are subsequently polymerized. The inside wall of the tube is treated with concentrated sulfuric acid to impart cation-exchange properties to the inside wall of the tube. The inside wall of the tubing can also comprise a polymer such as ABS, SIBS, or SBR that has been sulfonated. The volume of cavity 52 in the tube is controlled by piston 53 that can be actuated to press the tube against plate 54 to displace the solution in the cavity during the measurement of electrical conductivity of the ion-exchange material on the inside wall of the tube. When the pressure from the piston is removed, the tube inflates, and the sensor measures the conductivity of the solution in the inflated cavity. Both conductivity values are sensed by electrodes 55 and 56 positioned at the ends of the tube. Connection wire 57 is attached to each electrode. The electrodes are preferably corrosion-resistant metallic rings that fit over the end of a non-conductive, rigid tube 58 through which the solutions flow into and out of the sensor. A clamp 59 compresses the polymeric tube 51 tightly against the rigid tube 58 and the electrode rings 55 and 56 on both ends.

Figure 6:
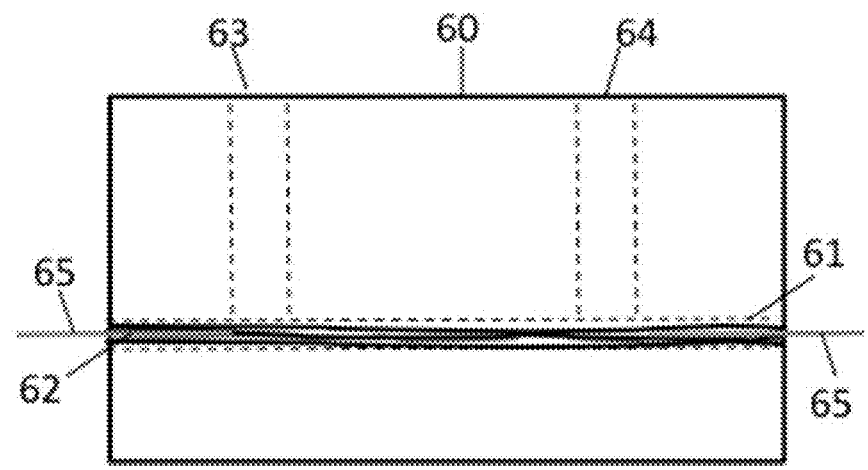
FIG. 6 is a cross-sectional view of a sensor made with fibers.

FIG. 6 illustrates a sensor in which the ion-conductive material is comprised of ion-exchange fibers. The body of the sensor is rigid plastic block 60. The block contains or forms hole 61 through which ion-exchange fibers 62 are inserted. Connected to fiber hole 61 are holes 63 and 64 through which the solution enters and exits the sensor. Imbedded in each end of the bundle of fibers 62 is electrode wire 65 that is in electrical contact with the fibers and with the electrical circuit for measuring the electrical conductivity of the fiber bundle. The ends of the fibers and the electrodes are preferably coated with a conductive adhesive (e.g., silver-filled epoxy) to enhance the electrical contact between the fibers and the electrodes. A benefit to the use of fibers is enhanced response to changes in solution composition. Because fiber diameter can be made very small compared with practical thickness of a membrane, the distance for ions to diffuse in the fiber can be short compared to diffusion distance in a membrane.

The configurations of the sensor described herein employ several configurations for reducing the effect of electrolyte solution on the measurement of the conductivity of the elongated ion-exchange material by either interrupting the path of the current or by reducing the volume of the cavity containing the solution. Another way for reducing the effect of electrolyte solution on the measurement is to drain the solution from the cavity before the measurement is made. Draining the solution is an alternative to the actuation of a diaphragm in FIG. 3 and FIG. 4. If the tubular sensor is drained before the conductivity measurement, the diaphragm can be eliminated, and the ion-exchange membrane can cover the entire wall of the tube. The electrodes can be positioned either on opposite sides of the tube, as shown in FIG. 4, or they can be positioned at the ends of the tube. The tubular design with the draining feature is a dual-function sensor. When the tube is full of solution, the measured conductivity reflects the conductivity of the solution, and when the solution is drained, the measured conductivity of the membrane reflects the ionic composition of the solution.

One of the advantages of the apparatus, devices, or methods described herein is that the sensor can detect changes in the conductivity of an elongated ion exchange material, and that conductivity can be interpreted as a change in the ratio of ions in the solution. Compared to the prior art of measuring the conductivity of a bed of ion-exchange particles, the measurement of which is confounded by the particle-to-particle contact and the conductivity of the fluid between the particles, the use of the device of the present invention eliminates the problem of particle-to-particle contact and minimizes or eliminates the problem of the parallel path of current flowing through the conductive fluid and results in an accurate measurement of the conductivity of the ion-exchange material in contact with the fluid. The tubular configuration with the diaphragm allows the measurement of ionic composition of the fluid as well as conductivity of the solution with a single pair of electrodes.

In addition to the use of a device described herein as a sensor for detecting hardness in the product water of a water softener, the present device or sensor has utility in detection of exhaustion of other ion-exchange devices. For example, the present invention can be used to detect exhaustion in the cation-exchange and anion-exchange resins used in demineralizers.

Figure 8:
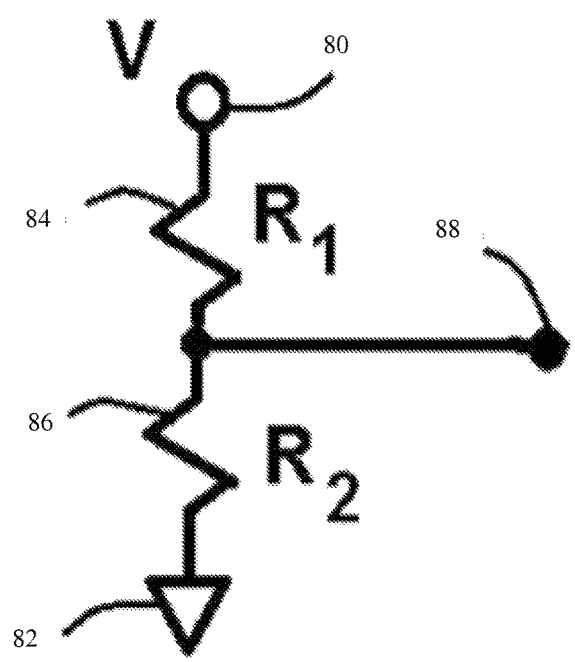
FIG. 8 depicts a voltage divider that is used to measure conductivity.

II. Electronic Processing of Membrane Sensor for Closed Loop Water Softener Control FIG. 8 depicts an electrical circuit known as a voltage divider. An arbitrary voltage, V, as referenced to a common node 82 is applied at node 80. Two resistors R1 84 and R2 86 are connected in electrical series between nodes 82 and 80. An electrical current flows through the series connection of resistors 84 and 86 that is given by equation 1.

$$I = \frac{V}{R_1 + R_2} \quad (1)$$

where I is electrical current in amperes. The voltage ($V_1$) at the node 88 between resistors 84 and 86 is given by voltage divider law as equation 2.

$$V_1 = \frac{VR_2}{R_1 + R_2} \quad (2)$$

If R1 84 is a known resistance, then a measurement of the voltage at the node 88 can be used together with the knowledge of the value of R1 84 to determine the value of R2 86 by the equation 3.

$$R_2 = \frac{V_1 R_1}{V - V_1} \quad (3)$$

Electrical conductance (or conductivity) is the reciprocal of electrical resistance (or resistivity), so the conductivity of R2 86 is easily calculated by taking the reciprocal. In an electronic circuit that is used to monitor the ionic conductivity of a sensor, the elongated ion-exchange material acts as resistance R2 86. It should be noted that the voltage V1 that is measured across this sensor can be used to calculate the resistance of the sensor by equation 3, calculating the conductance of the sensor by using equation 3 and then taking the reciprocal, or the voltage V1 can be used directly in a control scheme.

Although a series voltage divider is described where R1 84 is a fixed resistance connected on one end to node 80 and R2 86 is an elongated ion-exchange material that changes resistance with respect to ionic conductance from calcium atoms and is connected to common node 82, the two resistances could be swapped in position and the value of the sensor resistance calculated from the voltage divider law and knowledge of the fixed resistance value.

Figure 9:
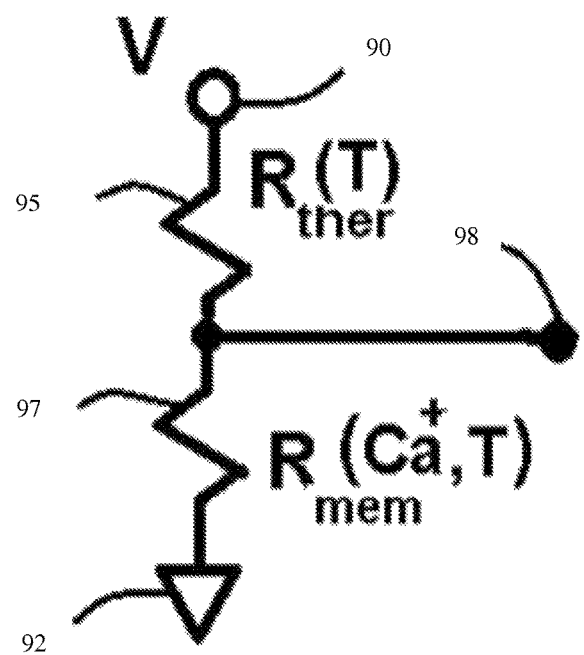
FIG. 9 depicts a voltage divider wherein the measured conductivity is temperature dependent and is compensated for by a thermistor.

FIG. 9 depicts a voltage divider consisting of an elongated ion-exchange material 97 in electrical series with a thermistor 95. A thermistor 95 is a device that changes in electrical resistance in a known way with changes in temperature. It is a temperature dependent device. The calcium-detecting sensor 97 changes resistance in response to the level of calcium in a fluid stream that contacts the sensor. But its resistance can also be sensitive to temperature, T. By placing the thermistor 95, having a resistance that changes in temperature in the same way that the ion-exchange material 97 changes with temperature, in thermal contact with the fluid stream, measurements from the sensor 97 can be desensitized with respect to temperature. Voltage measurements from the node 98 between the thermistor and the sensor will be proportional to the calcium level and will be insensitive to temperature variations.

Figures 10A, 10B:
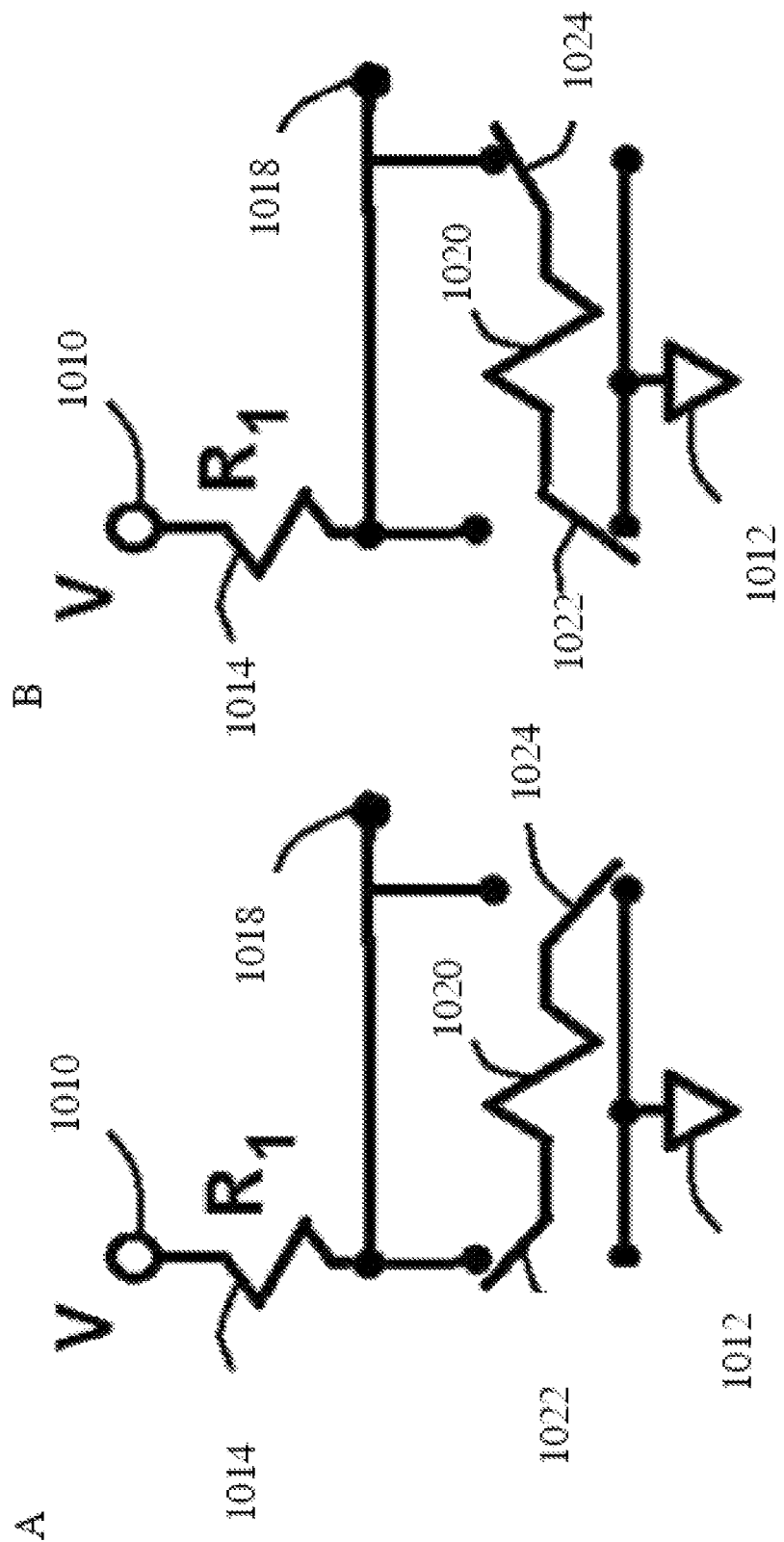
FIG. 10 depicts a circuit for periodically switching the polarity that is applied to the membrane of the elongated ion-exchange material.

One problem with applying the voltage divider law to determine sensor conductivity with a circuit like that in FIG. 8 is that the voltage across the sensor has an unchanging polarity. This results in a migration of ions on the elongated ion-exchange material to one end of the material and reduces its ability to correctly sense water hardness. FIG. 10 depicts a circuit that implements a voltage divider for detecting the value of resistance of an elongated ion-exchange material 1020 using a switched polarity approach. The switching is accomplished by a control algorithm. The purpose of the switching is to periodically reverse the polarity across the sensor 1020 using single pole double throw switches 1022, 1024 on either side of the sensor. Switches 1022 and 1024 are operated in lock step, that is, they are controlled to operate simultaneously. FIG. 10A depicts one polarity. By changing the state of both switches, electrical current is reversed through the sensor 1020 as in FIG. 10B. By periodically changing the state, there is a reduction in the net preferential migration of ions in either direction on the elongated ion-exchange material. Subsequent to the closure of switch 1022, 1024 in either the position in FIG. 10A or FIG. 10B, the voltage measured at node 1018 can be used to calculate the value of sensor resistance according to equation 3.

Figure 11:
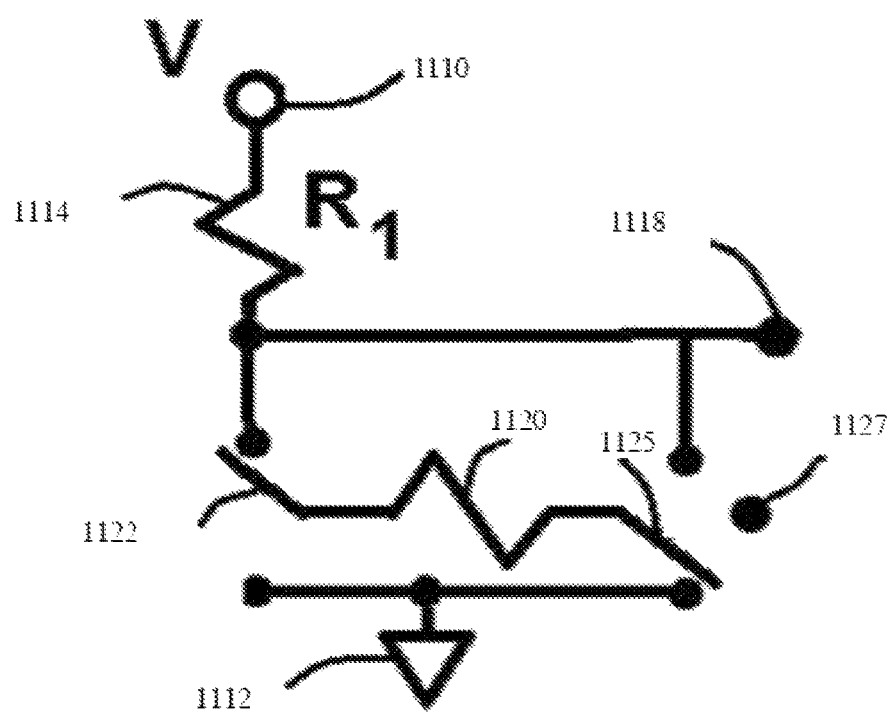
FIG. 11 depicts a circuit to control the application of electrical current to the membrane of the elongated ion-exchange material in either of two directions or to remove the flow of electrical current.

FIG. 11 depicts an embodiment in which one side of the sensor is attached to a single pole triple throw switch 1125. In this case, third position 1127 on triple throw switch 1125 can be an open node that does not have an electrical connection. By controlling switch 1125 to be in third position 1127, there would be zero external electrical current flowing through sensor 1120, which would prevent the migration of ions through the elongated ion-exchange material. The advantage to using a system like that depicted in FIG. 11 is that by independently controlling switches 1122 and 1125, it is possible to apply three states to sensor 1120. Either electrical current passes in one direction through sensor 1120 or it passes in the opposite direction or there is no electrical current flow.

Figure 12:
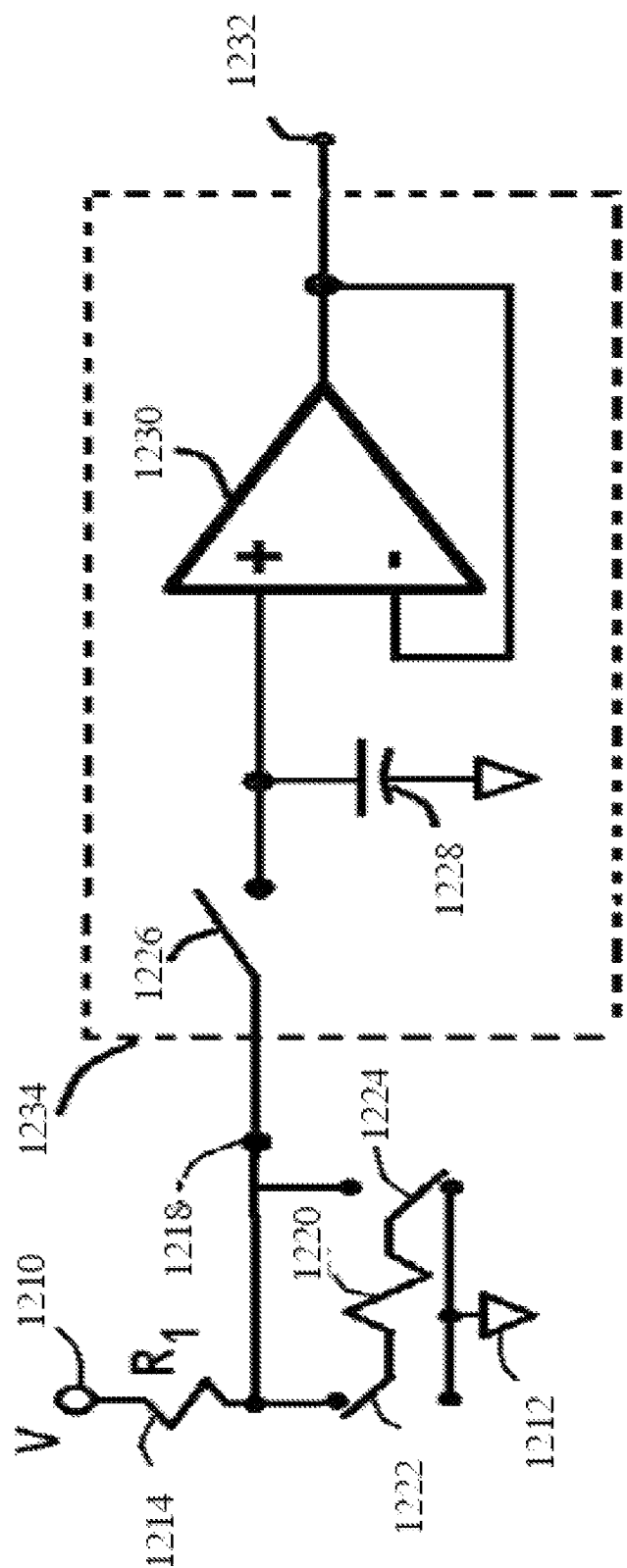
FIG. 12 depicts a circuit for latching a voltage output of known polarity that is proportional to resistance.

FIG. 12 depicts the use of a circuit called a sample and hold 1234 to latch measurements of sensor resistance. In this circuit, single pole single throw switch 1226 closes momentarily to connect from voltage divider node 1218 to charge capacitor 1228. Single pole single throw switch 1226 then opens, causing the voltage to be held constant on capacitor 1228. Operational amplifier 1230, connected in a so-called emitter follower configuration, has a very high input impedance and a very low output impedance, serving as a buffer to yield output 1232. The advantage to using switch 1226 to latch a voltage to output 1232 of the sample and hold 1234 is that when the positions of switches 1222 and 1224 are changing, the voltage at node 1218 may not be stable. So, switch 1226 can be controlled to allow modification of the output only when the input is stable. The voltage at output 1232 is representative of the membrane resistance and can be used in a control algorithm for managing water softening. The voltage at output 1232 is also representative of the conductance since electrical resistance and electrical conductance are reciprocals. If the voltage measurement for a given time sample, t, is v(t), this value and past measurements, v(t−1), v(t−2), etc can be used to construct a control algorithm.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 7:
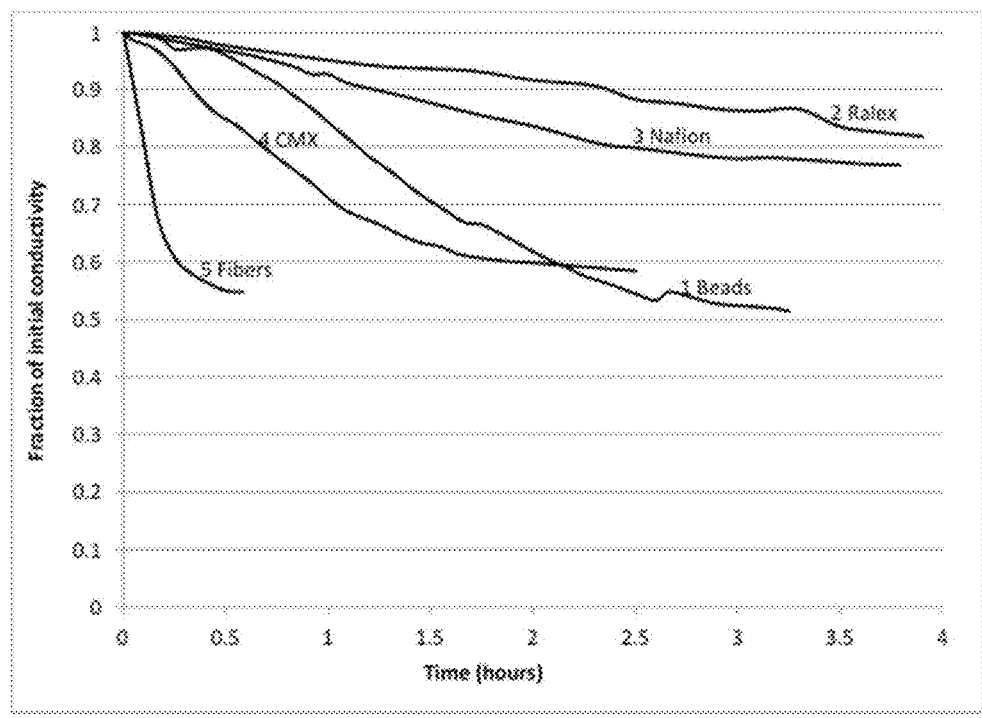
FIG. 7 illustrates data demonstrating the response of several configurations of hardness sensors.

Experiments were performed to demonstrate the response of several configurations of hardness sensors. In each case the sensor was equilibrated with a solution of NaCl that was adjusted to match the conductivity of local tap water. After equilibration, the sensor was exposed to tap water, and the conductivity of the sensor was measured as a function of time. The data were normalized by dividing the conductivity measured when the sensor was exposed to tap water by the conductivity when the sensor was exposed to NaCl solution. The flow rate was 4.1 ml/min for all experiments. Measurements were made with a Universal LCR Meter 878 (BK Precision) at 1 kHz. The data are plotted in FIG. 7.

As a reference for comparison to examples with elongated cation-exchange materials, a measurement was made of the change in conductivity of a strong-acid cation-exchange resin. The column of resin was 0.25" in diameter and 1" long with a 0.25" OD stainless steel tube as the electrodes. The conductivity of the resin bed decreased 20% in 68 minutes.

A 0.7-mm-thick cation-exchange membrane, Ralex CM-PES (MEGA), was tested in the planar sensor illustrated in FIG. 1. The conductivity decreased 20% in 480 minutes.

Nafion 117 membrane was tested in the planar sensor illustrated in FIG. 1. The conductivity decreased 20% in 150 minutes.

A 0.18-mm-thick cation-exchange membrane, Neosepta CMX, was tested in the planar sensor illustrated in FIG. 1. The conductivity decreased 20% in 40 minutes.

Cation-exchange fibers were tested in the sensor illustrated in FIG. 6. The conductivity decreased 20% in 6 minutes.

Although the invention has been described in detail with particular references to these preferred embodiments, other embodiments can achieve the same results. Variations and modifications of the present invention will be obvious to those skilled in the art, and it is intended to cover in the appended claims all such modifications and equivalents.

The invention claimed is:

1. A sensor for detecting a change in ionic composition of a fluid comprising:
   (i) a first non-conductive plate and a second non-conductive plate configured to form a cavity through which a test fluid flows,
   (ii) a continuous ion-exchange material positioned within the cavity configured to be in contact with the fluid,
   (iii) a first electrode in direct contact with a first portion of the continuous ion-exchange material and a second electrode in direct contact with a second portion of the continuous ion-exchange material so that there is a continuous electrical conductivity through the ion-exchange material between the two electrodes, the first and second electrode being separated by a predetermined distance, and
   (iv) a device coupled to the continuous ion-exchange material by the first and second electrodes that is configured for measuring the electrical conductivity of the continuous ion-exchange material.

2. The sensor of claim 1, wherein the continuous ion-exchange material is a membrane or fiber.

3. The sensor of claim 2, wherein the ion-exchange membrane is a cation-exchange membrane.

4. The sensor of claim 2, wherein the continuous ion-exchange material is an anion-exchange membrane.

5. The sensor of claim 1, wherein the non-conductive plates are planar.

6. The sensor of claim 1, wherein the sensor is configured as a non-conductive tube having an inner surface treated to impart ion exchange properties.

7. The sensor of claim 1, further comprising a diaphragm positioned in the cavity, said diaphragm being configured, upon application of pressure to the diaphragm, to displace fluid from the cavity for the purpose of eliminating the fluid as an alternative path for the flow of electric current between the electrodes.

8. The sensor of claim 7, wherein the diaphragm is coupled to an actuator.

9. The sensor of claim 8, wherein the actuator is an electrical, hydraulic, pneumatic, or mechanical actuator.

10. The sensor of claim 1, further comprising a flow regulation device configured to regulate fluid flow through the sensor.

11. A water softener system comprising a water softener apparatus fluidically connected to one or more sensors as described in claim 1.

12. The system of claim 11, wherein a sensor of claim 1 is positioned such that a portion of fluid exiting the water softener flows through the sensor.

13. The system of claim 11, wherein a sensor of claim 1 is positioned such that a portion of fluid flowing through the water softener flows through the sensor during transit through softener.

14. A water hardness sensor comprising (i) a first nonconductive plate and a second nonconductive plate configured to form a cavity through which a test fluid flows, wherein a surface of at least one of the plates facing the cavity is chemically modified to form an ion-exchange surface, (ii) a first electrode in contact with a first portion of the ion-exchange surface and a second electrode in contact with a second portion of the ion-exchange surface, the first and second electrode being separated by a predetermined distance, and (iii) a device for measuring the electrical conductivity across the ion-exchange surface operatively coupled to the first and second electrodes.

15. A water hardness sensor comprising (i) a non-conductive block that forms the housing for the sensor, said block forming a cavity; (ii) two or more ion-exchange fibers forming a fiber bundle are positioned in the cavity, wherein one end of the fiber bundle is in direct contact with a first electrode and the other end is in direct contact with a second electrode, the first and second electrode being separated by a predetermined distance, and (iii) and the first and second electrodes connected to a device for measuring the electrical conductivity across the ion-exchange fibers.

16. A method for detecting a change in ionic composition of a fluid comprising:
(a) measuring a first voltage at a first time point between electrodes coupled to a continuous ion-exchange material that is (i) passing an electrical current, (ii) in electrical series with a fixed resistance, and (iii) in contact with the fluid;
(b) measuring a second voltage at a second time point between electrodes coupled to a continuous ion-exchange material that is (i) passing an electrical current, (ii) in electrical series with a fixed resistance, and (iii) in contact with the fluid; and
(c) determining the change in ionic composition of the fluid based on a difference between the first and second voltage.

17. The method of claim 16, further comprising evacuating the fluid sample from the sensor after a predetermined period of time prior to measuring the first and second voltage.

18. A sensor for detecting a change in ionic composition of a fluid comprising:
(i) a first non-conductive plate and a second non-conductive plate configured to form a cavity through which a test fluid flows;
(ii) a continuous ion-exchange material positioned within the cavity configured to be in contact with the fluid;
(iii) a first electrode in direct contact with a first portion of the continuous ion-exchange material and a second electrode in direct contact with a second portion of the continuous ion-exchange material, the first and second electrode being separated by a predetermined distance;
(iv) a diaphragm positioned in the cavity, said diaphragm being configured, upon application of pressure to the diaphragm, to displace fluid from the cavity for the purpose of eliminating the fluid as an alternative path for the flow of electric current between the electrodes; and
(v) a device coupled to the continuous ion-exchange material by the first and second electrodes that is configured for measuring the electrical conductivity of the continuous ion-exchange material.

19. The sensor of claim 18, wherein the diaphragm is coupled to an actuator.

20. The sensor of claim 19, wherein the actuator is an electrical, hydraulic, pneumatic, or mechanical actuator.

* * * * *